(12) United States Patent
Axt et al.

(10) Patent No.: US 8,912,321 B2
(45) Date of Patent: *Dec. 16, 2014

(54) PREPARATION OF NUCLEOSIDES RIBOFURANOSYL PYRIMIDINES

(75) Inventors: Steven D. Axt, Menlo Park, CA (US); Keshab Sarma, Sunnyvale, CA (US); Justin Vitale, San Mateo, CA (US); Jiang Zhu, Cupertino, CA (US); Bruce Ross, Plainsboro, NJ (US); Suguna Rachakonda, Robbinsville, NJ (US); Quingwu Jin, San Jose, CA (US); Byoung-Kwon Chun, Robbinsville, NJ (US)

(73) Assignee: Gilead Pharmasset LLC, Foster City, CA (US)

(*) Notice: Subject to any disclaimer, the term of this patent is extended or adjusted under 35 U.S.C. 154(b) by 1296 days.

This patent is subject to a terminal disclaimer.

(21) Appl. No.: 12/444,608

(22) PCT Filed: Oct. 5, 2007

(86) PCT No.: PCT/US2007/021548
§ 371 (c)(1),
(2), (4) Date: Jul. 15, 2009

(87) PCT Pub. No.: WO2008/045419
PCT Pub. Date: Apr. 17, 2008

(65) Prior Publication Data
US 2010/0056770 A1    Mar. 4, 2010

Related U.S. Application Data

(60) Provisional application No. 60/850,962, filed on Oct. 10, 2006.

(51) Int. Cl.
*C07H 1/00* (2006.01)
*C07H 3/00* (2006.01)
*C08B 37/00* (2006.01)
*C07H 5/02* (2006.01)
*C07H 19/06* (2006.01)

(52) U.S. Cl.
CPC .. *C07H 5/02* (2013.01); *C07H 1/00* (2013.01); *C07H 19/06* (2013.01)
USPC ...................................................... 536/124

(58) Field of Classification Search
CPC ............. C07H 19/06; C07H 5/02; C07H 1/00
USPC ...................................................... 536/124
See application file for complete search history.

(56) References Cited

U.S. PATENT DOCUMENTS

| | | | |
|---|---|---|---|
| 6,348,587 B1 | 2/2002 | Schinazi et al. | |
| 6,846,810 B2 | 1/2005 | Martin et al. | |
| 6,911,424 B2 | 6/2005 | Schinazi et al. | |
| 7,105,499 B2 | 9/2006 | Carroll et al. | |
| 7,268,119 B2 | 9/2007 | Cook et al. | |
| 7,608,600 B2 | 10/2009 | Storer et al. | |
| 2004/0077587 A1 | 4/2004 | Sommadossi et al. | |
| 2005/0009737 A1 | 1/2005 | Clark | |
| 2006/0122146 A1 | 6/2006 | Chun et al. | |
| 2007/0167630 A1 * | 7/2007 | Imura et al. ................ | 546/281.7 |

FOREIGN PATENT DOCUMENTS

| | | |
|---|---|---|
| EP | 0136693 | 4/1985 |
| WO | 9943691 | 9/1999 |
| WO | 0109121 | 2/2001 |
| WO | 0190121 | 11/2001 |
| WO | 0192282 | 12/2001 |
| WO | 02057287 | 7/2002 |
| WO | 020057425 | 7/2002 |
| WO | 03026589 | 4/2003 |
| WO | 2004002422 | 1/2004 |
| WO | 2004002999 | 1/2004 |
| WO | 2004046331 | 6/2004 |
| WO | 2005003147 | 1/2005 |
| WO | 2005009418 | 2/2005 |
| WO | WO 2005/105807 A1 * | 11/2005 |
| WO | 2006012440 | 2/2006 |
| WO | WO2006012440 | 2/2006 |
| WO | WO2006031725 | 3/2006 |
| WO | 2006031725 | 6/2006 |

OTHER PUBLICATIONS

Kim, C.U., Misco, P.F. (1992) Facile, Highly Stereoselective Synthesis of 2',3'-Dideoxy- and 2',3'-Didehydro-2',3'-dideoxy Nucleosides via a Furanoid Glycal Intermediate. Tetrahedron Letters, vol. 33, No. 39, p. 5733-5736.*

(Continued)

*Primary Examiner* — Scarlett Goon
(74) *Attorney, Agent, or Firm* — Cozen O'Connor

(57) ABSTRACT

The present process provides an improved method for the preparation of 4-amino-1-((2R,3R,4R,5R)-3-fluoro-4-hydroxy-5-hydroxymethyl-3-methyl-tetrahydrofuran-2-yl)-1H-pyrimidin-2-one of the formula (IV) which is a potent inhibitor of Hepatitis C Virus (HCV) NS5B polymerase.

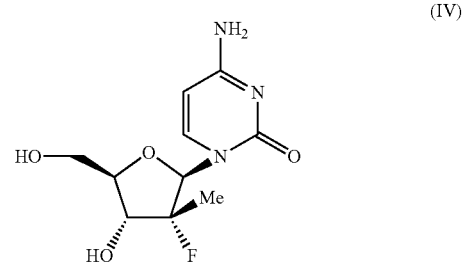

(IV)

7 Claims, No Drawings

(56) References Cited

OTHER PUBLICATIONS

Brown, H.C., Wetherill, R.B. (1996) "Sixty Years of Hydride Reductions" in Reductions in Organic Synthesis. ACS Symposium Series, p. 1-30.*

Harashim, S., Oda, O., Amemiya, S., Kojima, K. (1991) Sodium Bis(2-Methoxyethoxy)(1,1,1,3,3,3-Hexafluoro-2-propoxy)Aluminum Hydride, A New Stereoselective Reducing Agent in a Carbacyclin Synthesis. Tetrahedron, vol. 47, No. 16/17, p. 2773-2784.*

Szarek, W.A., Kong, X. (1997) "Direct Halogenation of Carbohydrate Derivatives" in Preparative Carbohydrate Chemistry, p. 105-125. Edited by Stephen Hanessian. Published by Marcel Dekker, Inc.*

McClinton, M.A. (1995) Triethylamine Tris(hydrogen fluoride): Applications in Synthesis. Aldrichimica Acta, vol. 28, No. 2, p. 31-34.*

"Alkenes and Potassium Manganate (VII)" [online] [Retrieved Dec. 16, 2011] Retrieved from the internet at <http://web.archive.org/web/20031013132018/http://www.chemguide.co.uk/organicprops/alkenes/kmno4.html> Published on Oct. 13, 2003.*

Karabinos, J.V. (1963) D-Gulonic-γ-Lactone. Organic Syntheses, Coll., vol. 4, p. 506.*

Greene, T.W. and wuts, P.G.M. (1991) Protective Groups in Organic Synthesis, published by John Wiley & Sons, Inc., p. 100-103.*

Wang, P., Chun, B.-K., Rachakonda, S., Du, J., Khan, N., Shi, J., Stec, W., Cleary, D., Ross, B.S., Sofia, M.J. (2009) An Efficient and Diastereoselective Synthesis of PSI-6130: A Clinically Efficacious Inhibitor of HCV NS5B Polymerase. Journal of Organic Chemistry, vol. 74, p. 6819-6824.*

International Search Report mailed Mar. 17, 2008 for related International App. No. PCT/US07/21548.

Helmut Vorbruggen, "Adventures in Silicon-Organic Chemistry", 28 Accounts of Chemical Research, pp. 509-520 (1995).

Clark et al., "Design, Synthesis and Antiviral Activity of 2'-Deoxy-2'-fluoro-2'-C-methycytidine, a potent inhibitor of HCV Replication", 48 J. Med. Chem., 5504-5508 (2005).

Pierra et al., "Synthesis and Pharmacokinetics of Valopicitabine (NM283), an Efficient Prodrug of the Potent Anti-HCV Agent 2'-C-Methylcytidine", 49 J. Med. Chem., 6614-6620 (2006).

Pogam et al., "No Evidence of R7128 Drug Resistance After Up to 4 Weeks Treatment of GT 1,2 and 3 Hepatitis C Virus Infected Individuals", from 44th Annual Meeting of the European Association for the Study of the Liver (EASL), Copenhagen, Denmark, Apr. 22-26, 2009.

Sofia et al., "R7128, A Potent and Selective Nucleoside Inhibitor of HCV NS5B Polymerase: An Overviewq of Clinical Efficacy and Progress Toward Second Generation Inhibitors", from HCV Drug Discovery 2008, chicago, IL., Apr. 28, 2008.

International Search Report mailed Jan. 30, 2007 for International App. No. PCT/EP06/069060.

Helmut Vorgruggen, "Adventures in Silicon—Organic Chemistry," Acc. Chem. Res., 1995, vol. 28, pp. 509-520.

* cited by examiner

PREPARATION OF NUCLEOSIDES RIBOFURANOSYL PYRIMIDINES

This application is a National Stage entry of international Application No. PCT/US 07/21548, filed Oct. 5, 2007, which claims priority to U.S. Provisional Application No. 60/850,962, filed Oct. 10, 2006, the disclosures of both of which are hereby incorporated by reference in their entirety.

The present invention relates to an improved process for the preparation of 4-amino-1-((2R,3R,4R,5R)-3-fluoro-4-hydroxy-5-hydroxymethyl-3-methyl-tetrahydrofuran-2-yl)-1H-pyrimidin-2-one of the formula

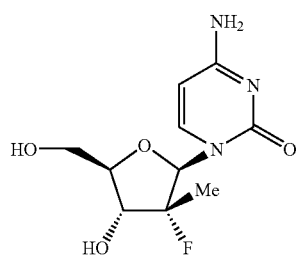

(IV)

which is a potent inhibitor of Hepatitis C Virus (HCV) NS5B polymerase.

The PCT Publication WO 2006/012440 discloses a process according to the scheme below. The process requires the burdensome separation of the anomers 14 and 16.

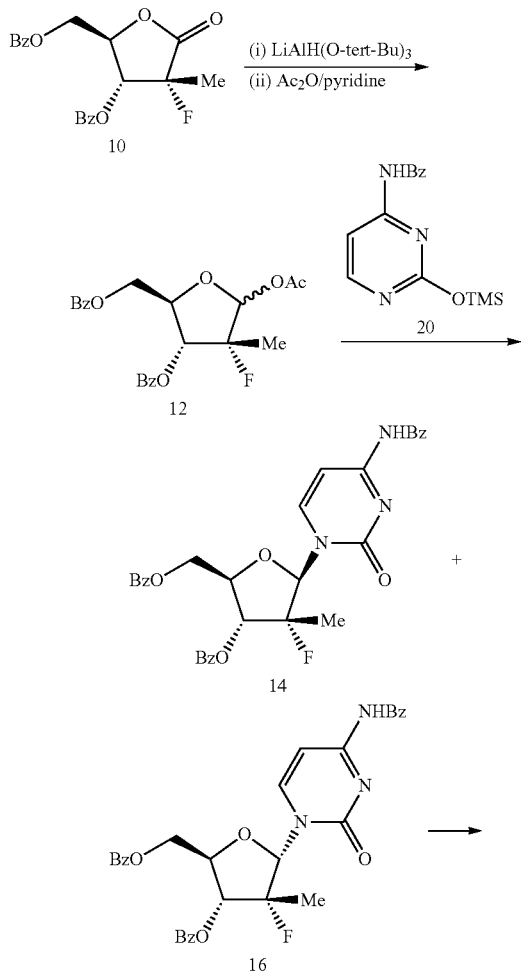

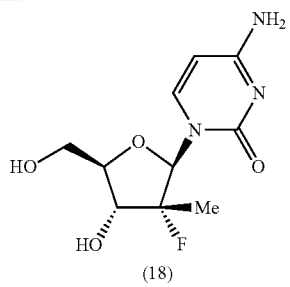

(18)

An object of the present invention is to provide an improved and scalable process for the preparation of 4-amino-1-((2R,3R,4R,5R)-3-fluoro-4-hydroxy-5-hydroxymethyl-3-methyl-tetrahydro-furan-2-yl)-1H-pyrimidin-2-one of the formula (IV)

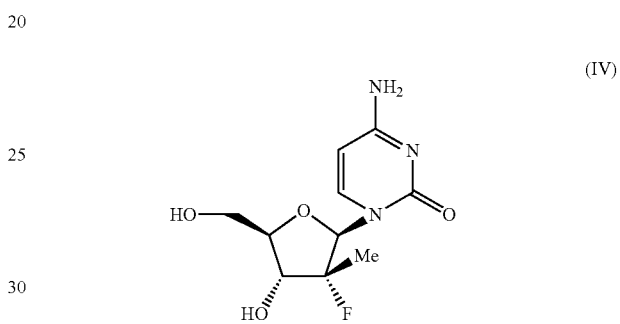

which avoids the drawbacks known in the art.

The process of the present invention comprises a) transforming an (aryl)alkanoic acid (2R,3R,4R)-2-(aryl) alkanoyloxymethyl-4-fluoro-4-methyl-5-oxo-tetrahydro-furan-3-yl ester of formula II

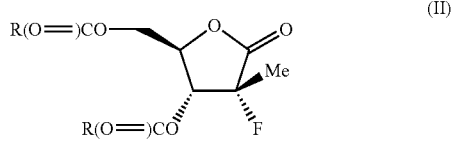

(II)

wherein R is aryl or alkyl into an (aryl)alkanoic acid (2R,3R,4R)-2-(aryl)alkanoyloxy methyl-5-chloro-4-fluoro-4-methyl-tetrahydro-furan-3-yl ester of formula III

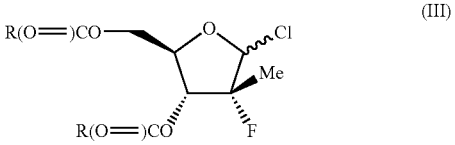

(III)

wherein R is aryl or alkyl;

b) converting the (aryl)alkanoic acid (2R,3R,4R)-2-(aryl) alkanoyloxy methyl-5-chloro-4-fluoro-4-methyl-tetrahydro-furan-3-yl ester of formula III into an(aryl)alkanoic acid (2R,3R,4R,5R)-3-(aryl)alkanoyloxy-5-(4-benzoylamino-2-oxo- 2Hpyrimidin-1-yl)-4-fluoro-4-methyl-tetrahydro-furan-2-ylmethyl ester of formula I

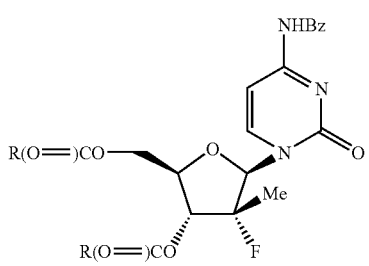

wherein R is aryl or alkyl and Bz is benzoyl and c) hydrolyzing the (aryl)alkanoic acid (2R,3R,4R,5R)-3-(aryl)alkanoyloxy-5-(4-benzoylamino-2-oxo-2H-pyrimidin-1-yl)-4-fluoro-4-methyl-tetrahydro-furan-2-ylmethyl ester of formula I to afford the 4-amino-1-((2R,3R,4R,5 5 R)-3-fluoro-4-hydroxy-5-hydroxymethyl-3-methyl-tetrahydro-furan-2-yl)-1H-pyrimidin-2-one of formula IV.

The term (aryl)alkanoic acid as used herein refers to a group $RCO_2H$ wherein R is either alkyl or aryl as those terms are defined herein. Correspondingly the term (aryl)alkanoic ester refers to a group $RCO_2R'$ where R is either alkyl or aryl. Most typically the R' represents the 3' and/or 5' position(s) of a ribose ring. The terms "(aryl)alkanoyl" and "(aryl)alkanoyloxy" refer to the groups RCO— and RCOO— respectively, where R is as described previously. The term "(aryl)alkanoyloxymethyl" group refers a group RCOOCH2- where R is as described previously.

The term "alkyl" as used herein denotes an unbranched or branched chain, saturated, monovalent hydrocarbon residue containing 1 to 10 carbon atoms.

The term "aryl" as used herein refers to phenyl group.

In a preferred embodiment of the present invention R has the meaning of phenyl.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The transformation in step a) comprises a reduction in the presence of a reducing agent and a subsequent chlorination in the presence of chlorinating agent.

Suitable reducing agent is sodium bis-(2-methoxyethoxy)(2,2,2-trifluoroethoxy)aluminum hydride which is commercially available under the tradename RedAl® as a solution in toluene.

The reduction usually takes place in an organic solvent such as in a halogenated hydrocarbon like dichloromethane at a reaction temperature of below 0° C., preferably below −5° C.

After completion of the reduction the reaction mixture is subjected to the chlorination reaction.

The chlorinating agent is as a rule selected from sulfuryl chloride, thionyl chloride or phosphorus oxychloride.

Preferably sulfuryl chloride in the presence of catalytic amounts of tetrabutyl ammonium bromide is used.

The chlorination is expediently performed at a reaction temperature between 0° C. and 40° C.

The (aryl)alkanoic acid (2R,3R,4R)-2-(aryl)alkanoyloxy methyl-5-chloro-4-fluoro-4-methyl-tetrahydro-furan-3-yl ester of formula III can be separated from the reaction mixture applying techniques known to the skilled in the art.

The conversion in step b) comprises reacting the (aryl)alkanoic acid (2R,3R,4R)-2-(aryl)alkanoyloxy methyl-5-chloro-4-fluoro-4-methyl-tetrahydro-furan-3-yl ester of formula III with O-trimethyl silyl-N4-benzoylcytosin in the presence of a Lewis acid.

The O-trimethyl silyl-N4-benzoylcytosin may be prepared in situ by reacting N-benzoyl cytosine with hexamethyldisilazan in the presence of ammonium sulfate in chlorobenzene under reflux conditions.

Common Lewis acids known in the art are suitable for the conversion in step b). Good results have been achieved with stannic chloride.

The reaction is usually performed at elevated temperature, for instance at about 70° C. until the coupling is complete.

The (aryl)alkanoic acid (2R,3R,4R,5R)-3-(aryl)alkanoyloxy-5-(4-benzoylamino-2-oxo-2H-pyrimidin-1-yl)-4-fluoro-4-methyl-tetrahydro-furan-2-ylmethyl ester of formula I so obtained can be separated from the reaction mixture applying techniques known to the skilled in the art.

The hydrolysis in step c) is performed in the presence of a base.

Suitable bases are organic bases like alkali metal alkoxides. Preferably sodium methoxide in methanol as solvent is used.

The reaction is performed at elevated temperature, for instance at about 50° C. until the hydrolysis is complete.

The 4-amino-1-((2R,3R,4R,5R)-3-fluoro-4-hydroxy-5-hydroxymethyl-3-methyltetrahydro-furan-2-yl)-1H-pyrimidin-2-one of the formula IV can be isolated following methods known to the skilled in the art.

In a further embodiment of the present invention a process for the preparation of the starting product, the (aryl)alkanoic acid (2R,3R,4R)-2-(aryl)alkanoyloxymethyl-4-fluoro-4-methyl-5-oxo-tetrahydro-furan-3-yl ester of formula II

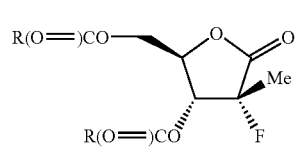

wherein R is phenyl has been developed.

The process comprises the steps a1) transforming the (E)-3-((S)-2,2-dimethyl-[1,3]dioxolan-4-yl)-2-methyl-acrylic acid ethyl ester of formula V

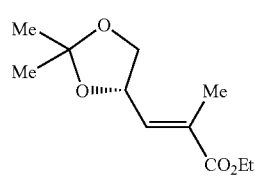

into the (2S,3R)-3-((R)-2,2-dimethyl-[1,3]dioxolan-4-yl)-2,3-dihydroxy-2-methyl propionic acid ethyl ester of formula VI

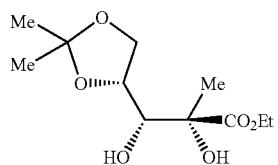

b1) converting the (2S,3R)-3-((R)-2,2-dimethyl-[1,3]di-oxolan-4-yl)-2,3-dihydroxy-2-methyl-propionic acid ethyl ester of formula VI into the sulfite of formula VII (VII)

c1) further reacting the sulfite of formula VII to the sulfate of formula VIII (VIII)

d1) transforming the sulfate of formula VIII into the fluorohydrin sulfate of formula IX (IX)

e1) decomposing the fluorohydrin sulfate of formula IX into the lactone of formula X (X)

and finally f1) acylating the lactone of formula X to form the end product of formula II wherein R is phenyl.

The present process can be described with SCHEME A below:

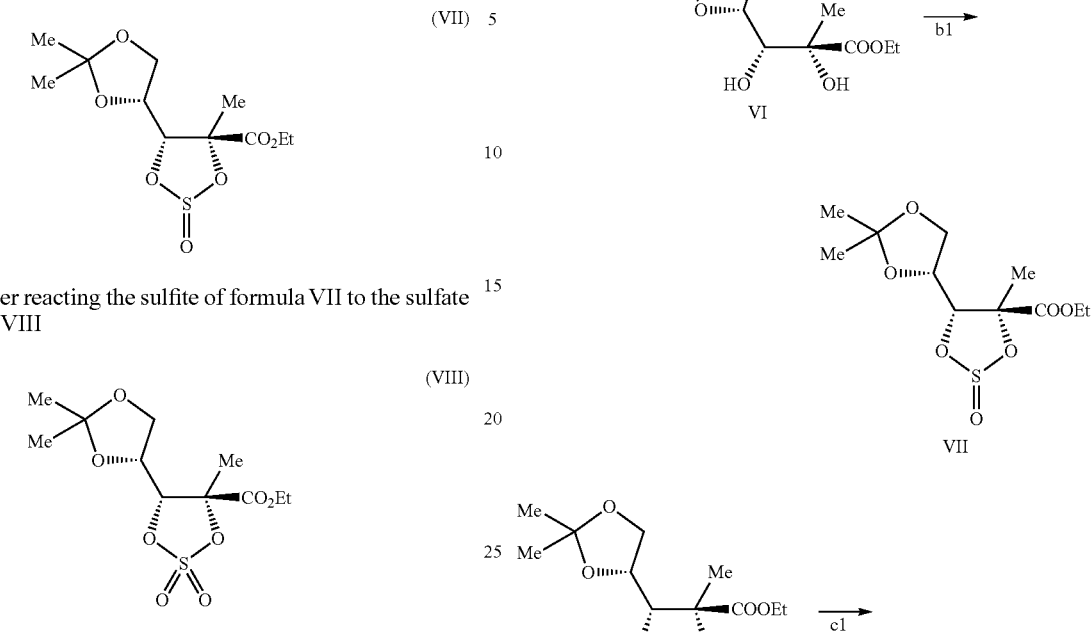

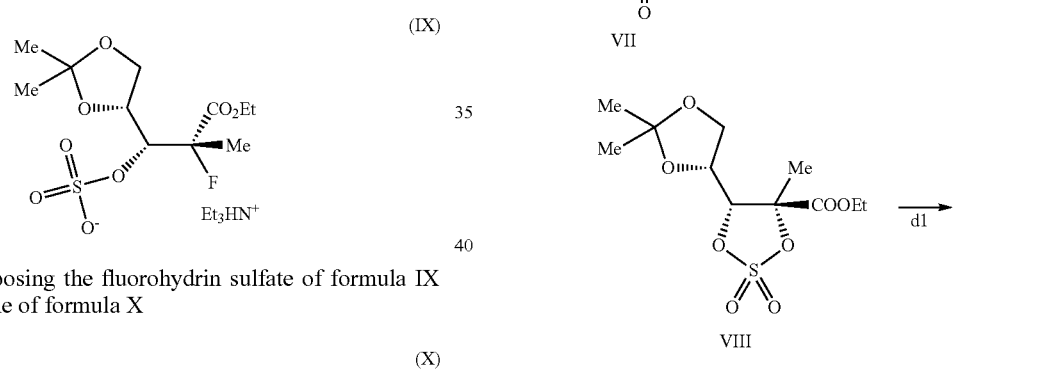

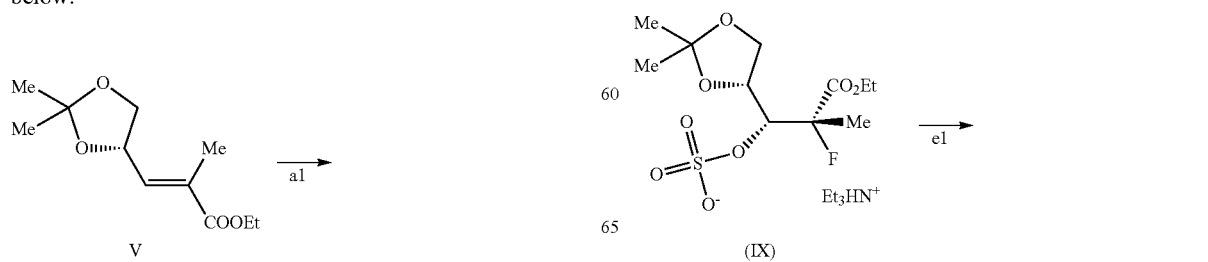

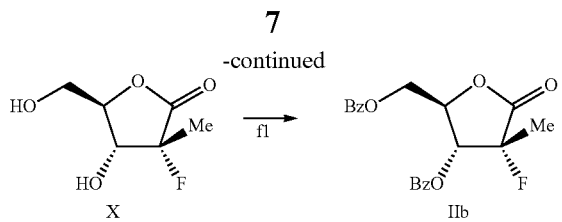

(a1) acetone-NaMnO4 (aq), ethylene glycol, NaHCO3, -10 to 0° C.; aq. NaHSO3 (quench); (b1) i-PrOAc, MeCN, TEA, SOCl2; (c1) i-PrOAc, MeCN, NaOCl; (d1) TEA-3HF, TEA; (e1) HCl (aq)-BaCl2-aq; (f1) (PhCO)2O, DMAP, MeCN.

The asymmetric hydroxylation in step a1) was discovered to be best carried out with sodium permanganate in the presence of ethylene glycol, sodium bicarbonate in acetone at a temperature of −20 to 0° C. which afforded the diol in 60-64% on pilot plant scale. Starting compound (V) can be obtained from (1S,2S)-1,2-bis-((R)-2,2-dimethyl-[1,3]dioxolan-4-yl)-ethane-1,2-diol (C. R. Schmid and J. D. Bryant, Jerry D., Org. Syn. 1995 72:6-13) by oxidative cleavage of the diol and treating the resulting aldehyde with 2-(triphenyl-$\lambda^5$-phosphanylidene)-propionic acid ethyl ester.

The cyclic sulfate (VIII) can be prepared by cyclization of the vicznal diol with e.g. thionyl chloride in step b1) and oxidation of the resulting cyclic sulfite (VII) in step c1) to the corresponding sulfate (VIII) with NaOCl in the presence of MeCN. It has been found that the cyclic sulfates can be stabilized during processing by the addition of a trialkylamine such as TEA or DIPEA at 2-10 mole % relative to the cyclic sulfate. Differential scanning calorimetry (DSC) showed a shift in the onset of decomposition from approximately 110 to 180° C. when 3.5 mole % of DIPEA was added to (VIII). Contacting (VIII) with triethylamine-trihydrofluoride/TEA in step d1) affords the sulfated fluorohydrin (IX) which in the presence of water affords the fluorohyrin (X) An improved yield of (X) can be obtained in step d1) when BaCl2 is incorporated in the reaction mixture to scavenge the liberated sulfate. Under the acidic conditions concomitant hydrolysis of the acetonide liberates a triol which spontaneously cyclizes to the γ-lactone (X). Contacting (X) with benzoic anhydride and DMAP in step f1) affords the dibenzoate of the lactone (IIb) which is used in the glycosylation step.

While the benzoyl protecting group (R=phenyl) is preferred, other potential protecting groups selected from methoxymethyl, methoxyethyl, benzyloxymethyl, ethoxymethyl, trityl, triethylsilyl, t-butyldimethylsilyl, t-butyldiphenylsilyl, acyl including acetyl, pivaloyl, benzoyl, toluoyl, 4-phenyl benzoyl, 2-, 3-, or 4-nitrobenzoyl, 2-, 3-, or 4-chlorobenzoyl, other substituted benzoyl may be applied. The base used for step f1) includes, but is not limited to the following list: imidazole, pyridine, DMAP, TEA, DIPEA, 1,4-diazabicyclo[2,2,2]octane. The solvent used for step f1) includes, but is not limited to acetonitrile, pyridine, DCM, chloroform, DCE, THF.

EXAMPLES

The abbreviations used include: 1,2-dichloroethane (DCE), dichloromethane (DCM), di-iso-propylethylamine (DIPEA), N,N-dimethyl acetamide (DMA), 4-N,N-dimethylaminopyridine (DMAP), ethanol (EtOH), ethylacetate (EtOAc), methanol (MeOH), methyl (Me), ethyl (Et), isopropanol (IPA), acetonitrile (MeCN), phenyl (Ph), room temperature (rt or RT), triethylamine (TEA or Et3N), tetrahydrofuran (THF).

Example 1

Benzoic acid 3-benzoyloxy-5-(4-benzoylamino-2-oxo-2H-pyrimidin-1-yl)-4-fluoro-4-methyl-tetrahydro-furan-2-ylmethyl ester (14)

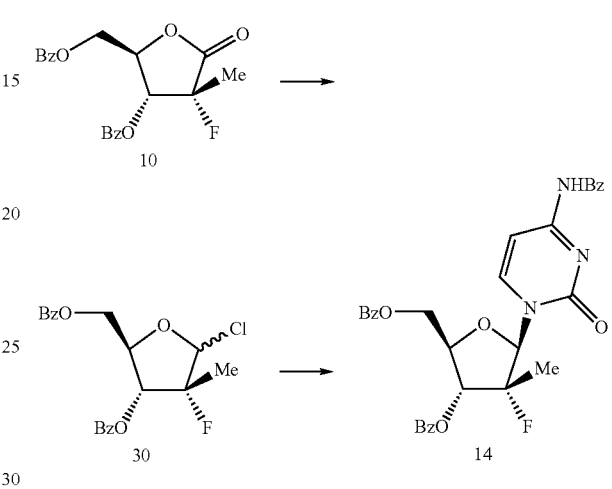

Trifluoroethanol (4.08 kg) is added slowly to a cold solution (−15° C.) of RED-AL® solution (12.53 kg) and toluene (21.3 kg) while maintaining the reaction temperature at or below −10° C. After warming up to ambient temperature (ca. 20° C.), the modified RED-AL reagent mixture (30.1 kg out of the 37.6 kg prepared) is added slowly to a pre-cooled solution (−15° C.) of fluorolactone dibenzoate 10 (10 kg) in DCM (94.7 kg) while maintaining reaction temperature at or below −10° C. After reduction of the lactone (monitored by in-process HPLC), catalytic amounts of tetrabutylammonium bromide (90 g) is added to the reaction mixture. Sulfuryl chloride (11.86 kg) is then added while maintaining reaction temperature at or below 0° C. The reaction mixture is then heated to 40° C. until formation of the chloride is complete (ca. 4 h) or warmed to ambient temperature (20-25° C.) and stirred over night (ca. 16 h). The reaction mixture is cooled to about 0° C., and water (100 L) is added cautiously while maintaining reaction temperature at or below 15° C. The reaction mixture is then stirred at ambient temperature for ca. 1 h to ensure hydrolytic decomposition of excess sulfiryl chloride and the phases are separated. The organic layer is washed with a dilute solution of citric acid (prepared by dissolving 15.5 kg of citric acid in 85 L of water) and then with dilute KOH solution (prepared by dissolving 15 kg of 50% KOH in 100 L of water). The organic phase is then concentrated and solvents are replaced with chlorobenzene (2×150 kg) via atmospheric replacement distillation. The resulting solution containing 30 is dried azeotropically.

A suspension of N-benzoyl cytosine (8.85 kg), ammonium sulfate (0.07 kg) and hexamethyldisilazane (6.6 kg) in chlorobenzene (52.4 kg) is heated to reflux (ca. 135° C.) and stirred (ca. 1 h) until the mixture becomes a clear solution. The reaction mixture is then concentrated in vacuo to obtain the O-trimethyl silyl-N4-benzoylcytosin as a syrupy liquid. The anhydrous solution of 30 in chlorobenzene (as prepared) and stannic chloride (28.2 kg) are added to this concentrate.

The reaction mixture is maintained at about 70° C. until the desired coupling reaction is complete (ca. 10 h) as determined by in process HPLC. Upon completion, the reaction mixture is cooled to ambient temperature and diluted with DCM (121 kg). This solution is added to a suspension of solid NaHCO$_3$ (47 kg) and CELITE® (9.4 kg) in DCM (100.6 kg). The resulting slurry is cooled to 10-15° C., and water (8.4 kg) is added slowly to quench the reaction mixture. The resulting suspension is very slowly (caution: gas evolution) heated to reflux (ca. 45° C.) and maintained for about 30 min. The slurry is then cooled to ca. 15° C., and filtered. The filter cake is repeatedly reslurried in DCM (4×100 L) and filtered. The combined filtrate is concentrated under atmospheric pressure (the distillate collected in the process is used for reslurrying the filter cake) until the batch temperature rises to about 90° C. and then allowed to cool slowly to about −5° C. The resulting slurry is aged for at least 2 h at −5° C.

The precipitated product is filtered and washed with IPA (30 kg+20 kg), and oven-dried in vacuo at about 70° C. to afford 8.8 kg (57.3%) of 1-(2-deoxy-2-fluoro-2-methyl-3-5-O-dibenzoyl-β-D-ribofuranosyl)-N-4-benzoylcytosine (14, CAS Reg No. 817204-32-3) which was 99.3% pure.

Example 2

4-Amino-1-(3-fluoro-4-hydroxy-5-hydroxymethyl-3-methyl-tetrahydro-furan-2-yl)-1H-pyrimidin-2-one (18)

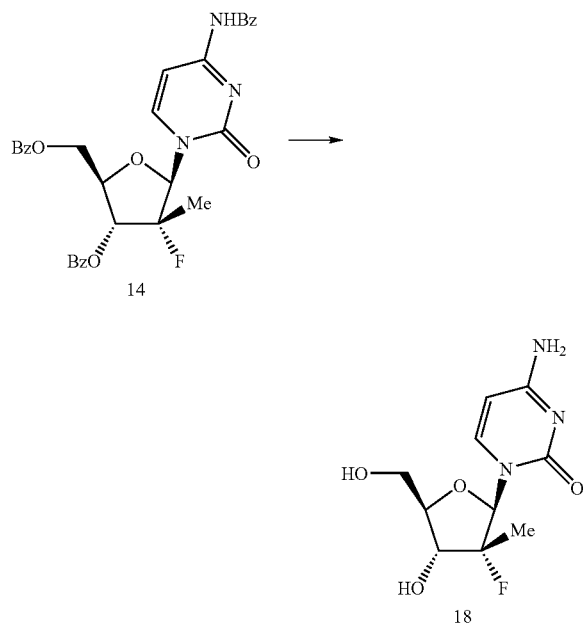

A slurry of 14 (14.7 kg) in MeOH (92.6 kg) is treated with catalytic amounts of methanolic sodium methoxide (0.275 kg). The reaction mixture is heated to ca. 50° C. and aged (ca. 1 h) until the hydrolysis is complete. The reaction mixture is quenched by addition of isobutyric acid (0.115 kg). The resulting solution is concentrated under moderate vacuum and then residual solvents are replaced with IPA (80 kg). The batch is distilled to a volume of ca. 50 L. The resulting slurry is heated to ca. 80° C. and then cooled slowly to ca. 5° C. and aged (ca. 2 h). The precipitated product is isolated by filtration, washed with IPA (16.8 kg) and dried in an oven at 70° C. in vacuo to afford 6.26 kg (88.9%) of 18 which assayed at 99.43% pure Example 3

(2S,3R)-3-[(4R)-2,2-dimethyl-[1,3]dioxolan-4-yl]-2,3-dihydroxy-2-methyl-propionic acid ethyl ester (24)

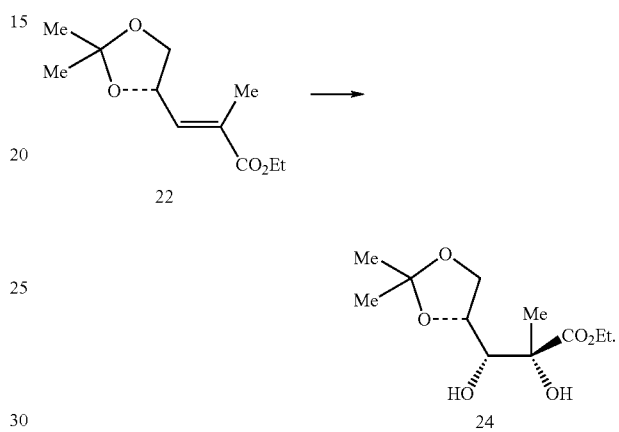

A suspension of 22 (10 kg, CAS Reg. No. 81997-76-4), ethylene glycol (11.6 kg), solid NaHCO$_3$ (11.8 kg) and acetone (150 L) is cooled to ca. −15° C. A solution of 36% aqueous NaMnO4 (19.5 kg) is charged slowly (over 4 h) to the suspension maintaining reaction temperature at or below −10° C. After stirring for 0.5 h at −10° C., an aliquot of the reaction mixture (ca. 5 mL) is quenched with 25% aqueous sodium bisulfite (ca. 15 mL). A portion of resulting slurry is filtered and submitted for GC analysis to check the progress of the reaction. When the reaction is complete, the reaction mixture is quenched by slow (over 40 min) addition of cooled (ca. 0° C.) 25% aqueous NaHSO$_3$ (60 L). The temperature of the reaction mixture is allowed to reach 4° C. during the quench. CELITE® (ca. 2.5 kg) is then slurried in acetone (8 kg) and added to the dark brown reaction mixture. The resulting slurry is aged at ambient temperature to obtain light tan slurry. The slurry is filtered, and the filter cake is washed with acetone (3×39 kg). The combined filtrate is concentrated by vacuum distillation (vacuum approximately 24 inches of Hg (ca. 810 mbar); max pot temperature is 32° C.) to remove the acetone. The aqueous concentrate is extracted with EtOAc (3×27 kg), and the combined organic extracts were washed with water (25 L). The organic phase is then concentrated by atmospheric distillation and EtOAc is replaced with toluene. The volume of the batch is adjusted to ca. 20 L. Heptane (62 kg) is added and the batch cooled to ca. 27° C. to initiate crystallization. The batch is then cooled to −10° C. After aging overnight at −10° C., the product is filtered, washed with 10% toluene in heptane and dried at 50° C. under vacuum to afford 6.91 kg (59.5%) of 24 (CA RN 81997-76-4) as a white crystalline solid.

Example 4

(3R,4R,5R)-3-Fluoro-4-hydroxy-5-hydroxymethyl-3-methyl-dihydro-furan-2-one (10)

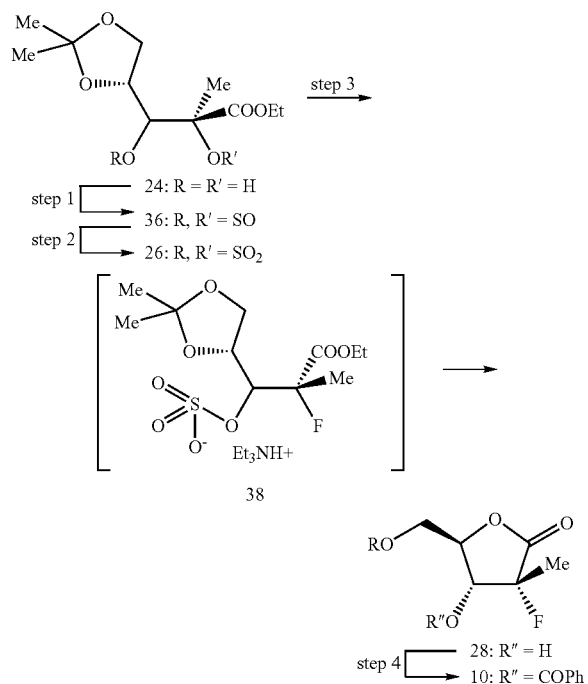

Steps 1 & 2—A dry, clean vessel was charged with 24 (6.0 kg), isopropyl acetate (28.0 kg), MeCN (3.8 kg) and TEA (5.4 kg). The mixture was cooled to 5-10° C., and thionyl chloride (3.2 kg) was added slowly while cooling the solution to maintain the temperature below 20° C. The mixture was stirred until no starting material was left (GC analysis). The reaction was typically complete within 30 min after addition is complete. To the mixture was added water (9 kg) and after stirring, the mixture was allowed to settle. The aqueous phase was discarded and the organic phase was washed with a mixture of water (8 kg) and saturated NaHCO$_3$ (4 kg) solution. To the remaining organic phase containing 36 was added MeCN (2.5 kg) and solid NaHCO$_3$ (3.1 kg). The resulting slurry was cooled to ca. 10° C. Bleach (NaOCl solution, 6.89 wt % aqueous solution, 52.4 kg, 2 eq.) was added slowly while cooling to maintain temperature below 25° C. The mixture was aged with stirring over 90-120 min at 20-25° C., until the reaction was complete (GC analysis). After completion of the reaction, the mixture was cooled to ca. 10° C. and then quenched with aqueous Na$_2$SO$_3$ solution (15.1% w/w, 21 kg) while cooling to maintain temperature below 20° C. The quenched reaction mixture was filtered through a cartridge filter to remove inorganic solids. The filtrate was allowed to settle, and phases are separated and the aqueous phase is discarded. The organic layer was washed first with a mixture of water (11 kg) and saturated NaHCO$_3$ solution (4.7 kg), then with of saturated NaHCO$_3$ solution (5.1 kg). DIPEA (220 mL) was added to the organic phase and the resulting solution was filtered through CELITE® (bag filter) into a clean drum. The reactor was rinsed with isopropyl acetate (7 kg) and the rinse is transferred to the drum. The organic phase was then concentrated under vacuum ca. 850-950 mbar while maintaining reactor jacket temperature at 45-50° C. to afford 26 as an oil (~10 L). Additional DIPEA (280 mL) was added and the vacuum distillation was continued (jacket temperature 50-55° C.) until no more distillate was collected. (Batch volume ca. 7 L).

Step 3—To the concentrated oil from step 2 containing 26 was 5 added TEA (2.34 kg) and TEA-trihydrofluoride (1.63 kg). The mixture was heated to 85° C. for 2 h. The batch was sampled to monitor the progress of the reaction by GC. After the reaction was complete conc. HCl (2.35 kg) was added to the mixture and the resulting mixture heated to ca. 90° C. (small amount of distillate collected). The reaction mixture was stirred at ca. 90° C. for 30 min and then saturated aqueous BaCl$_2$ solution (18.8 kg) was added. The resulting suspension was stirred at about 90° C. for 4 h. The resulting mixture was then azeotropically dried under a vacuum (9-10 inches of Hg) by adding slowly n-propanol (119 kg) while distilling off the azeotropic mixture (internal batch temperature ca. 85-90° C.). To the residual suspension was added toluene (33 kg) and vacuum distillation was continued to distill off residual n-propanol (and traces of water) to a minimum volume to afford 28.

Step 4—To the residue from step 3 containing 28 was added MeCN (35 kg) and ca. 15 L was distilled out under atmospheric pressure. The reaction mixture was cooled to ca. 10° C. and then benzoyl chloride (8.27 kg) and DMAP (0.14 kg) are added. TEA (5.84 kg) was added slowly to the reaction mixture while cooling to maintain temperature below 40° C. The batch was aged at ca. 20° C. and the progress of the benzoylation is monitored by HPLC. After completion of the reaction, EtOAc (30 kg) was added to the mixture and the resulting suspension is stirred for about 30 min. The reaction mixture was filtered through a CELITE® pad (using a nutsche filter) to remove inorganic salts. The solid cake was washed with EtOAc (38 kg). The combined filtrate and washes were washed successively with water (38 kg), saturated NaHCO$_3$ solution (40 kg) and saturated brine (44 kg). The organic phase was polish-filtered (through a cartridge filter) and concentrated under modest vacuum to minimum volume. IPA (77 kg) was added to the concentrate and ca. 25 L of distillate was collected under modest vacuum allowing the internal batch temperature to reach ca. 75° C. at the end of the distillation. The remaining solution was then cooled to ca. 5° C. over 5 h and optionally aged overnight. The precipitate was filtered and washed with of cold (ca. 5° C.) IPA (24 kg). The product was dried under vacuum at 60-70° C. to afford 6.63 kg (70.7% theory of 10 which was 98.2% pure by HPLC.

The invention claimed is:
1. A process for the preparation of 4-amino-1-((2R,3R,4R,5R)-3-fluoro-4-hydroxy-5-hydroxymethyl-3-methyl-tetrahydro-furan-2-yl)-1H-pyrimidin-2-one of formula IV

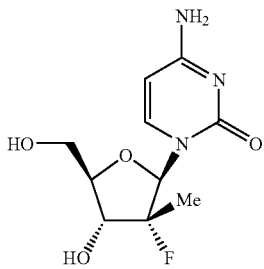

(IV)

comprising
a) transforming a compound of formula II

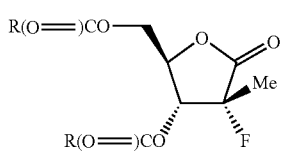

wherein R is aryl or alkyl
into a compound of formula III

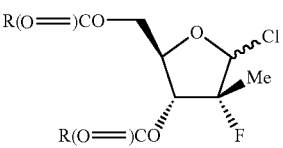

wherein R is aryl or alkyl,
wherein the transformation comprises a reduction in the presence of a reducing agent and a subsequent chlorination in the presence of a chlorinating agent;
b) converting the compound of formula III into a compound of formula I

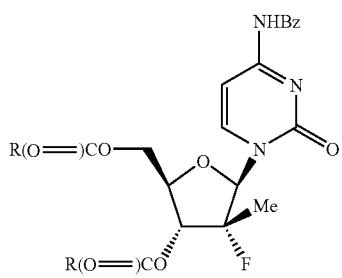

wherein R is aryl or alkyl and Bz is benzoyl,
wherein the conversion comprises reacting the compound of formula III with O-trimethyl silyl-N4-benzoylcytosine in the presence of a Lewis acid; and
c) hydrolyzing the compound of formula I to afford the 4-amino-1-((2R,3R,4R,5 5R)-3-fluoro-4-hydroxy-5-hydroxymethyl-3-methyl-tetrahydro-furan-2-yl)-1H-pyrimidin-2-one of formula IV,
wherein the hydrolysis is performed in the presence of a base.

2. The process according to claim 1, characterized in that R has the meaning of phenyl.

3. The process according to claim 1, characterized in that the reducing agent is sodium bis-(2-methoxyethoxy)(2,2,2-trifluoro-ethoxy)aluminum hydride.

4. The process according to claim 1, characterized in that the chlorinating agent is sulfuryl chloride, thionyl chloride, or phosphorus oxychloride.

5. The process according to claim 4, characterized in that the chlorinating agent is sulfuryl chloride in the presence of catalytic amounts of tetrabutylammonium bromide.

6. The process according to claim 1, comprising the preparation of the compound of formula II

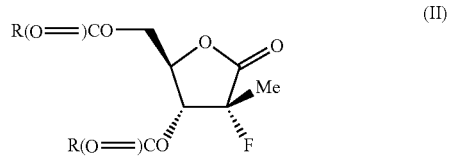

wherein R is phenyl,
comprising the steps of
a1) transforming a compound of formula V

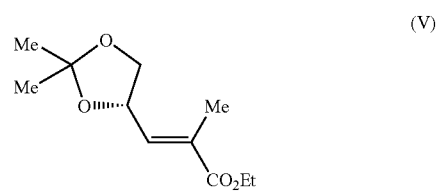 [SMILES: CCOC(=O)/C(C)=C/[C@H]1COC(C)(C)O1]

into a compound of formula VI

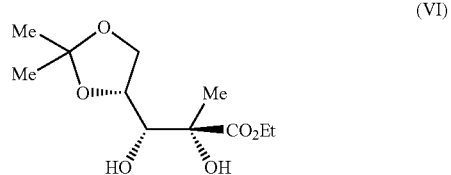 [SMILES: CCOC(=O)[C@@](C)(O)[C@H](O)[C@H]1COC(C)(C)O1]

wherein the transformation is performed with sodium permanganate in the presence of ethylene glycol and sodium bicarbonate;
b1) converting the compound of formula VI into a sulfite of formula VII

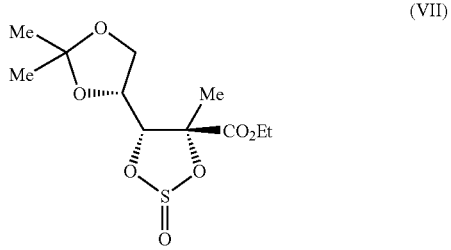

wherein the conversion is performed with thionylchloride;
c1) further reacting the sulfite of formula VII to yield a sulfate of formula VIII

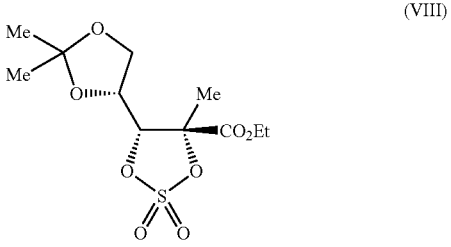 [SMILES: CCOC(=O)[C@@]1(C)OS(=O)(=O)O[C@@H]1[C@H]1COC(C)(C)O1]

wherein the reaction is performed with sodium hypochlorite;

d1) transforming the sulfate of formula VIII into a fluorohydrin sulfate of formula IX

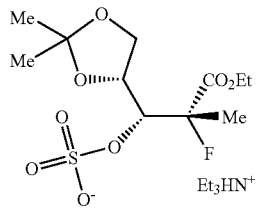

(IX)

wherein the transformation is performed with a trialkylamine;

e1) decomposing the fluorohydrin sulfate of formula IX into a lactone of formula X

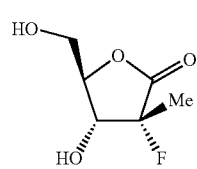

(X)

wherein the decomposition is performed with barium chloride in water;

and finally f1) acylating the lactone of formula X to form the end product of formula II, wherein R is phenyl, wherein the acylation is performed with benzoic anhydride.

7. The process according to claim 6, wherein the trialkylamine is triethylamine together with triethylamine-trihydrofluoride.

* * * * *